United States Patent [19]

Preston et al.

[11] 4,045,439

[45] Aug. 30, 1977

[54] 6-SUBSTITUTED-4-HYDROXYCINNOLIN-3-YL CARBOXYLIC ACIDS AND ESTERS THEREOF

[75] Inventors: John Preston; Austin John Reeve, both of Macclesfield, England

[73] Assignee: Imperial Chemical Industries Limited, London, England

[21] Appl. No.: 626,531

[22] Filed: Oct. 28, 1975

[30] Foreign Application Priority Data

Nov. 7, 1974 United Kingdom .............. 48205/74

[51] Int. Cl.$^2$ ......................................... C07D 237/28
[52] U.S. Cl. ................................. 260/250 C; 424/250
[58] Field of Search ..................... 424/250; 260/250 C

[56] References Cited

U.S. PATENT DOCUMENTS 2,797,218  6/1957  Barber et al. .................. 260/250 C

FOREIGN PATENT DOCUMENTS 46-22028  2/1969  Japan
1,306,839  2/1973  United Kingdom

OTHER PUBLICATIONS

Barber et al. J. Chem. Soc (c) 1967, p. 1657.

*Primary Examiner*—Donald G. Daus
*Assistant Examiner*—Mark L. Berch
*Attorney, Agent, or Firm*—Cushman, Darby & Cushman

[57] ABSTRACT

6-Substituted-4-hydroxycinnolin-3-yl carboxylic acids and esters thereof, processes for their preparation, and pharmaceutical compositions comprising any one of these compounds. A representative compound is ethyl 6-glycylamino-4-hydroxycinnolin-3-yl carboxylate hydrochloride. The compounds are active as inhibitors of effects following the combination of reagin-like antibodies and their antigens.

5 Claims, No Drawings

6-SUBSTITUTED-4-HYDROXYCINNOLIN-3-YL CARBOXYLIC ACIDS AND ESTERS THEREOF

This invention relates to heterocyclic compounds, and more particularly it relates to new cinnoline derivatives which are active as inhibitors of the effects following the combination of reagin-like antibodies and their antigens. Furthermore, as stated below, some of the said new cinnoline derivatives are also useful as intermediates.

According to the invention there are provided cinnoline derivatives of the formula:

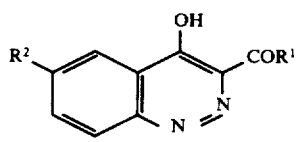

I wherein $R^1$ stands for a hydroxy, $C_{1-6}$-alkoxy, $C_{3-6}$-alkoxyalkoxy, $C_{7-10}$-phenylalkoxy or phenoxy radical, and $R^2$ stands for an amino (—$NH_2$), $C_{2-6}$-alkanoyl, cyano, carboxy, $C_{1-5}$-alkylthio, $C_{1-5}$-alkylamino, di-$C_{1-5}$-alkylamino, cycloalkylamino of not more than 6 carbon atoms, 2,2-dimethyl-5-oxo-cyclohexenylamino, 2-hydroxy-2-phenylethylamino, 2-nitroethylenylamino, $C_{2-20}$-alkanoylamino, benzamido, nitrobenzamido, ($C_{2-4}$-alkanoyloxy)benzamido, ($C_{1-3}$-alkoxy)benzamido, di-($C_{1-3}$-alkoxy)benzamido, tri-($C_{1-3}$-alkoxy)benzamido, benzenesulphonamido, p-toluenesulphonamido, ($C_{1-3}$-alkane)sulphonamido, ($C_{1-3}$-alkoxy)carbonylamino, polyhalogeno($C_{1-3}$-alkoxy)carbonylamino, benzyloxycarbonylamino, ($C_{1-5}$-alkyl)xanthone-3-carbonylamino, glycylamino, N,N-dimethylglycylamino, alanylamino, valylamino, phenylalanylamino, aspartylamino, β-alanylamino, phenylglycylamino, $N^2$-($C_{1-5}$-alkyl)ureido, $N^2$-[($C_{2-5}$-alkoxycarbonyl)(benzyl)methyl]ureido, $N^2$-phenylureido, $N^2$-monohalogenophenylureido, $N^2$-dihalogenophenylureido, $N^2$-phenylthioureido, thioureylene (-NH.CS.NH-), nitrophenyl, ($C_{2-5}$-alkoxycarbonyl)phenyl of 2,5-dioxopyrrolin-3-yl radical, or an aromatic heterocyclic radical of 5 or 6 ring atoms and containing a nitrogen, oxygen or sulphur atom as a ring atom and which heterocyclic radical may optionally be substituted by a $C_{1-3}$-alkyl or aldehydo radical or by a halogen atom, and pharmaceutically-acceptable salts thereof, but excluding 6-amino-4-hydroxycinnolin-3-yl carboxylic acid and pharmaceutically-acceptable salts thereof.

It is to be understood that the compounds of the formula I can exist in the tautomeric cinnolone form having the formula:

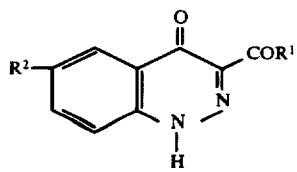

II wherein $R^1$ and $R^2$ have the meanings stated above, but for convenience they will all be referred to as 4-hydroxycinnoline derivatives in this specification.

Suitable halogeno substituents (see above) are fluorine, chlorine and bromine atoms.

As a suitable value for $R^1$ there may be mentioned, for example, a hydroxy, methoxy, ethoxy, 2-ethoxyethoxy, benzyloxy or phenoxy radical.

As a suitable value for $R^2$ there may be mentioned, for example, an amino, acetyl, cyano, carboxy, methylthio, isopropylamino, n-butylamino, n-but-2-ylamino, dimethylamino, cyclopentylamino, cyclohexylamino, 2,2-dimethyl-5-oxocyclohexenylamino, 2-hydroxy-2-phenylethylamino, 2-nitroethylenylamino ($O_2N.CH=CH.NH—$), acetylamino, hexanoylamino, palmitoylamino, benzamido, p-nitrobenzamido, o-acetoxybenzamido, 3,4,5-trimethoxybenzamido, p-toluenesulphonamido, methanesulphonamido, 2,2,2-trichloroethoxycarbonylamino, benzyloxycarbonylamino, 7-isopropylxanthone-3-carbonylamino, glycylamino, N,N-dimethylglycylamino, D-alanylamino, L-valylamino, L-phenylalanylamino, L-aspartylamino, β-alanylamino, β-phenylglycylamino, $N^2$-methylureido, $N^2$-[methoxycarbonyl(benzyl)methyl]ureido, $N^2$-phenylureido, $N^2$-p-chlorophenylureido, $N^2$-2,4-dibromophenylureido, $N^2$-phenylthioureido, thioureylene, nitrophenyl, ethoxycarbonylphenyl, 2,5-dioxopyrrolin-3-yl, furyl, 2-aldehydofuryl, thienyl, pyridyl, 2-chloropyridyl or 4-methylpyridyl radical.

As one particular embodiment of the invention there may be mentioned the compounds of the formula I wherein $R^1$ has the meaning stated above and $R^2$ stands for a cyano, carboxy, cycloakylamino of not more than 6 carbon atoms, 2,2-dimethyl5-oxocyclohexenylamino, 2-hydroxy-2-phenylethylamino, 2-nitroethylenylamino, $C_{2-20}$-alkanoylamino, benzamido, nitrobenzamido, ($C_{2-4}$-alkanoyloxy)benzamido, ($C_{1-3}$-alkoxy)benzamido, di-($C_{1-3}$-alkoxy)benzamido, tri-($C_{1-3}$-alkoxy)benzamido, benzenesulphonamido, p-toluenesulphonamido, ($C_{1-3}$-alkane)sulphonamido, ($C_{1-3}$-alkoxy)carbonylamino, polyhalogeno($C_{1-3}$-alkoxy)carbonylamino, benzyloxycarbonylamino, ($C_{1-5}$-alkyl)xanthone-3-carbonylamino, glycylamino, N,N-dimethylglycylamino, alanylamino, valylamino, phenylalanylamino, aspartylamino, β-alanylamino, phenylglycylamino, $N^2$-($C_{1-5}$-alkyl)ureido, $N^2$-[($C_{2-5}$-alkoxycarbonyl)(benzyl)methyl]ureido, $N^2$-phenylureido, $N^2$-monohalogenophenylureido, $N^2$-dihalogenophenylureido, $N^2$-phenylthioureido, thioureylene, or 2,5-dioxopyrrolin-3-yl radical, or an aromatic heterocyclic radical of 5 or 6 ring atoms and containing a nitrogen, oxygen or sulphur atom as a ring atom and which heterocyclic radical may optionally be substituted by a $C_{1-13}$-alkyl or aldehydo radical or by a halogen atom, and pharmaceutically-acceptable salts thereof.

A sub-group of compounds of the invention which are preferred because of their high oral activity are compounds of the formula I wherein $R^1$ stands for a hydroxy or $C_{1-3}$-alkoxy radical and $R^2$ stands for a $C_{1-5}$-alkylthio radical, or a $C_{3-5}$-alkylamino radical of the formula alkyl$^1$(alkyl$^2$)CH.NH— wherein alkyl$^1$ and alkyl$^2$ may be the same or different, for example an isopropylamino or n-but-2-ylamino radical, or a cyclopentylamino or cyclohexylamino, 2-nitroethylenylamino, N,N-dimethylglycylamino, D-alanylamino, L-phenylalanylamino, L-aspartylamino, β-alanylamino, $N^2$-phenylthioureido, nirophenyl, thienyl, 4-methylpyridyl or 2-chloropyridyl radical, and pharmaceutically acceptable salts thereof.

Specific compounds of the invention which are particularly preferred because of the their high activity are ethyl 6-cyclopentylamino-4-hydroxycinnolin-3-yl carboxylate, ethyl 4-hydroxy-6-isopropylaminocinnolin-3-yl carboxylate, ethyl 4-hydroxy-6L-phenylalanylaminocinnolin-3-yl carboxylate and ethyl 4-hydroxy-6-thienylcinnolin-3-yl carboxylate, and pharmaceutically-acceptable acid-addition salts thereof.

Suitable salts of the invention in the case where the compounds of the formula I are sufficiently basic are acid-addition salts derived from inorganic or organic acids affording pharmaceutically-acceptable anions, for example hydrochlorides or citrates. Suitable salts in the case where the compounds of the formula I are sufficiently acidic, for example wherein $R^1$ stands for a hydroxy radical, are salts wherein the anion is derived from the said compound of the formula I and the cation is pharmaceutically-acceptable. Examples of such salts are ammonium, alkali metal, alkaline earth metal or aluminium salts, or a salt with a pharmaceutically-acceptable organic base, for example N-methylglucamine, triethanolamine or 2-amino-2-hydroxy-methyl-1,3-propanediol. These salts are all obtainable by conventional chemical means.

The compounds of the invention wherein $R^1$ has the meaning stated above and $R^2$ stands for a nitrophenyl, ($C_{2-5}$-alkoxycarbonyl) phenyl or 2,5-dioxopyrrolin-3-yl radical, or an aromatic heterocyclic radical of 5 or 6 ring atoms and containing a nitrogen, oxygen or sulphur atom as a ring atom, and which heterocyclic radical may optionally be substituted by a $C_{1-3}$-alkyl or aldehydo radical or by a halgen atom, and pharmaceutically-acceptable salts thereof, are obtainable by a process which is believed to be a non-analogy process inasmuch as it appears that no directly comparable process has been described in the prior art. The said process comprises first diazotising a compound of the formula I in which $R^1$ has the meaning stated above and $R^2$ stands for an amino radical, and then reacting the resulting diazonium salt with a compound of the formula $R^2H$, wherein $R^2$ stands for nitrophenyl, ($C_{2-5}$-alkoxycarbonylphenyl) or 2,5-dioxopyrrolin-3-yl radical or an aromatic heterocyclic radical of 5 or 6 ring atoms and containing a nitrogen, oxygen or sulphur atom as a ring atom and which heterocyclic radical may optionally be substituted by a $C_{1-3}$-alkyl or aldehydo radical or by a halogen atom.

The diazotisation may be carried out by any known procedure, for example by means of nitrous acid in an acidic aqueous medium at approximately 0° C., or by means of an alkyl nitrite of not more than 6 carbon atoms, for example amyl nitrite. An advantage of using an alkyl nitrite for the diazotisation is that in many cases both the diazotisation and the subsequent step can be carried out using the compound of the formula $R^2H$ as both reactant and solvent. The second step of this process may, if desired, be accelerated or completed by the application of heat.

Apart from the exception discussed immediately above, the compounds of the invention are all obtainable by the use of known general chemical processes (i.e. by the use of so-called analogy processes). The various processes for the preparation of the compounds of the invention constitute further features of this invention.

Compounds of the formula I wherein $R^1$ has the meaning stated above and $R^2$ stands for an amino radical are obtained by reducing the corresponding compound wherein $R^2$ stands for a nitro group. The reduction may, for example, be carried out by the use of hydrogen and a suitable hydrogenation catalyst, for example palladium-on-charcoal, in the presence of a suitable solvent, for example a $C_{1-5}$-alkanol, for example ethanol.

Compounds of the formula I wherein $R^1$ has the meaning stated above and $R^2$ stands for a $C_{2-6}$-alkanoyl radical are obtained by oxidising the corresponding compound wherein $R^2$ stands for a $C_{2-6}$-alkyl radical, for example an ethyl radical. A suitable oxidising agent is chromium trioxide in concentrated sulphuric acid.

Compounds of the formula I wherein $R^1$ has the meaning stated above and $R^2$ stands for an acylamino radical (the latter being interpreted broadly and including, besides alkanoylamino and aroylamino radicals, alkoxycarbonylamino, arenesulphonamido and alkanesulphonamido radicals, for example) are obtained by acylating the corresponding compound wherein $R^2$ stands for an amino radical. The acylating agent may be, for example, the appropriate acid halide, for example an acid chloride, or it may be the appropriate acid anhydride, and the process may optionally be carried out in an appropriate solvent, for example pyridine.

Compounds of the formula I wherein $R^1$ has the meaning stated above and $R^2$ stands for a cyano radical are obtained by diazotising the corresponding compound wherein $R^2$ stands for an amino radical, and reacting the resulting diazonium salt with cuprous cyanide.

Compounds of the formula I wherein $R^1$ and $R^2$ stand for a carboxy radical are obtained by hydrolysing the corresponding compound wherein $R^1$ has the meaning stated above and $R^2$ stands for a cyano radical. A suitable hydrolytic agent is an inorganic acid, or an alkali metal hydroxide optionally in the presence of hydrogen peroxide.

Compounds of the formula I wherein $R^1$ has the meaning stated above and $R^2$ stands for an aminoacylamino radical, for example a glycylamino or D-alanylamino radical, are obtained by removing the protecting radical from the corresponding protected aminoacylamino derivative. The protecting radical may be, for example, a benzyloxycarbonyl radical, which is removed by hydrogenolysis using hydrogen and a suitable catalyst, for example palladium-on-charcoal.

Compounds of the formula I wherein $R^1$ has the meaning stated above and $R^2$ stands for a dimethylamino radical are obtained by reacting the corresponding compound wherein $R^2$ stands for an amino radical with formaldehyde and formic acid.

Compounds of the formula I wherein $R^1$ has the meaning stated above and $R^2$ stands for a $C_{3-5}$-alkylamino radical of the formula —$NHCHR^3R^4$, wherein $R^3$ stands for hydrogen or an alkyl radical and $R^4$ stands for an alkyl radical, or $R^2$ stands for a cycloalkylamino radical of not more than 6 carbon atoms, are obtained by reacting the corresponding compound of the formula I wherein $R^2$ stands for an amino radical with the appropriate carbonyl compound, for example acetone or cyclopentanone, under reducing conditions. The reducing conditions may be provided by the use of hydrogen and a suitable hydrogenation catalyst, for example a platinum catalyst, or by the use of an alkali metal borohydride.

Compounds of the formula I wherein $R^1$ has the meaning stated above and $R^2$ stands for a N,N-dimethylglycylamino radical are obtained by reacting the corresponding compound wherein $R^2$ stands for a glycylamino radical with hydrogen and formaldehyde in the presence of a suitable hydrogenation catalyst, for example palladium-on-charcoal.

Compounds of the formula I wherein $R^1$ has the meaning stated above and $R^2$ stands for a 2-hydroxy-2-phenylethylamino radical are obtained by reacting the corresponding compound wherein $R^2$ stands for an amino radical with styrene oxide, optionally in the presence of a suitable solvent, for example ethanol.

Compounds of the formula I wherein $R^1$ stands for a $C_{1-6}$-alkoxy, $C_{3-6}$-alkoxyalkoxy, $C_{7-10}$-phenylalkoxy or phenoxy radical, and $R^2$ stands for a substituted ureido or thio-ureido radical are obtained by reacting the corresponding compound wherein $R^2$ stands for an amino radical with the appropriate isocyanate or isothiocyanate. The reaction is conveniently carried out in a suitable solvent, for example pyridine.

Compounds of the formula I wherein $R^2$ stands for a $C_{1-5}$-alkylthio radical are obtained by diazotising the corresponding compound wherein $R^2$ stands for an amino radical, and then reacting the diazonium salt with an appropriate alkali metal alkyl xanthate, for example potassium methyl xanthate, and then decomposing the xanthate so obtained by heating it in the presence of a suitable solvent, for example toluene.

Compounds of the formula I wherein $R^1$ has the meaning stated above and $R^2$ stands for a 2-nitroethylenylamino radical are obtained by reacting the corresponding compound wherein $R^2$ stands for an amino radical with methazonic acid $(HO.N=CH.CH_2.NO_2)$ in the presence of dilute hydrochloric acid.

The above-mentioned biological activity of the compounds of this invention has been demonstrated by their ability to inhibit, in the rat, passive cutaneous anaphylaxis induced by reagin-like antibodies to egg albumin, using Bordetella pertussis as an adjuvant. This is a known meaningful test. The activity of individual compounds of this invention in the test depends upon their precise chemical structure, but generally speaking the compound exhibit activity at an intravenous dose of 0.2 to 20 mg./kg. No toxic effects or undesirable side effects have been observed with the compounds at doses at which they are active in the above-mentioned test. One particularly important feature of the majority of the compounds of the invention is that they are active orally.

When a compound of the invention is used in a warm-blooded mammal, for example man, for the treatment of intrinsic (non-allergic) asthma or a disease or syndrome which is initiated by an antigen-antibody reaction, for example allergic asthma, hay fever, urticaria or an auto-immune disease, it is recommended that the said compound be administered either (a) by inhalation at a dose of 001 mg./kg. to 1 mg./kg. at appropriate intervals, for example at 6-hourly intervals during the day, or (b) intravenously at a total daily dose of 25 mg. per man, or (c) orally at a dose of 5 mg./kg. to 250 mg./kg. at appropriate intervals, for example at 6-hourly intervals during the day, or (d) as a suppository at a dose of 5 to 250 mg.

According to a further feature of the invention there are provided pharmaceutical compositions comprising a cinnoline derivative of the formula I, wherein $R^1$ and $R^2$ have the meanings stated above, or a pharmaceutically-acceptable salt thereof, and an inert pharmaceutically-acceptable diluent or carrier.

The pharmaceutical compositions of the invention are obtainable by well known methods using conventional diluents or carriers. The compositions may be in the form of an orally-administrable unit dosage form, for example a tablet or capsule, and more particularly a tablet containing 5 to 50 mg. of the cinnoline derivative of the invention. Alternatively, they may be in a form adapted for administration by inhalation, for example a solution or suspension in an aqueous or non-aqueous medium, which is administered by inhalation using a conventional nebulizer or a pressurised container, for example an aerosol dispenser, for example a breath-actuated aerosol dispenser. Alternatively, the compositions may comprise a mixture of the active ingredient with a solid diluent or carrier, for example lactose, the said mixture being in a fine particulate form suitable for administration by inhalation using a powder inhalatin device. Alternatively, the compositions may be in a form adapted for intravenous administration, for example a sterile solution or suspension. Alternatively, the compositions may be in the form of a suppository.

The pharmaceutical compositions of the invention may contain, in addition to a cinnoline derivative which characterises this invention, one or more of the following known compounds:

compounds which are known to be useful in the treatment of asthma and which are selected from:

(a)

i. bronchodilators, for example atropine or a β-adrenergic stimulant, for example isoprenaline, adrenaline, salbutamol, orciprenaline or isoethacine;

ii. corticosteroids, for example beclomethasone dipropionate or betamethasone valerate; and iii. phosphodiesterase inhibitors for example theophylline or aminophylline; and (b)

i. α-adrenergic blocking agents, for example phentolamine;

ii. prostaglandin $E_1$ or $E_2$;

iii. 3-acetamido-6-methyl-8-n-propyl-s-triazolo[4,3-a]pyrazine;

iv. 2-amino-4,6-di-$C_{1-4}$-alkyl-4,5-dihydro-5-oxo-s-triazolo[1,5-a]pyrimidines; and v. 6,8-di-$C_{1-4}$-alkyl-5,6-dihydro-5-oxo-s-triazolo[4,3-c]pyrimidines.

The pharmaceutical compositions of the invention may contain from 1 to 50% by weight of a compound of the formula I or a pharmaceutically-acceptable salt thereof.

As indicated above and in the Examples, the compounds of the formula I wherein $R^2$ stands for an amino radical are useful as intermediates, as well as being useful by virtue of their biological activity.

The invention is illustrated but not limited by the following Examples:

EXAMPLE 1

A suspension of ethyl 4-hydroxy-6-nitrocinnolin-3-yl carboxylate (5.26 g.) and 30% w/w palladium-on-charcoal catalyst (0.5 g.) in ethanol (800 ml.) was stirred in an atmosphere of hydrogen at a slight overpressure and room temperature for 16 hours, by which time the uptake of hydrogen had ceased. The suspension was warmed to boiling on a steam bath, filtered hot through celite (20 g.), and the filtrate was evaporated under reduced pressure. Benzene (300 ml.) was added to the residual solid, and then evaporated under reduced pressure; this process was repeated. The residual solid was ethyl 6-amino-4-hydroxycinnolin-3-yl carboxylate, m.p. 230°–232° C.

The nitro ester used as starting material was obtained as follows:

Ethanol (200 ml.) was stirred at −40° C. and thionyl chloride (15 ml.) was added dropwise during 5 minutes. After a further 10 minutes at −40° C., 4-hydroxy-6-nitrocinnolin-3-yl carboxylic acid (10 g.) was added. The mixture was stirred overnight and allowed to warm to room temperature. The suspension was heated under reflux on a steam bath for 1 hour, and then kept at 0° C. for several hours. The solid was filtered off, and washed successively with ethanol (2 × 30 ml.) and ether (100 ml.) to give ethyl 4-hydroxy-6-nitrocinnolin-3-yl carboxylate, m.p. 294°–296° C.

EXAMPLE 2

A solution of ethyl 6-ethyl-4-hydroxycinnolin-3-yl carboxylate (5.0 g.) in concentrated sulphuric acid (30 ml.) was stirred at 10° C. as chromium trioxide (6.0 g.) was added. The solution was stirred at room temperature for 5 hours and then was poured onto cracked ice. The resulting aqueous solution was extracted with ethyl acetate (4 × 250 ml.), and the combined extracts were shaken with excess sodium bisulphite solution to extract ketonic material as the bisulphite compound. The aqueous bisulphite solution was washed with ethyl acetate (2 × 250 ml.), and then treated with excess 40% v/v formaldehyde in water and sodium bicarbonate solution. The aqueous solution was extracted with ethyl acetate (3 × 250 ml.) and the combined extracts were dried (MgSO$_4$), and filtered. Evaporation of the filtrate yielded a solid residue which on recrystallisation from a mixture of ethanol and ether gave ethyl 6-acetyl-4-hydroxycinnolin-3-yl carboxylate, m.p. 250°–252° C.

EXAMPLE 3

A mixture of ethyl 6-benzyloxycarbonylglycylamino-4-hydroxycinnolin-3-yl carboxylate (0.55 g.), 30% w/w palladium-on-charcoal catalyst (0.05 g.) and N-hydrochloric acid (1.3 ml.) was shaken in an atmosphere of hydrogen for 24 hours, after which time a solid had precipitated. The suspension was boiled, and water was added to dissolve the solid. The catalyst was removed by filtration of the hot mixture, and the filtrate was evaporated to dryness under reduced pressure. The residual solid was recrystallised from a mixture of ethanol and ethyl acetate to give ethyl 6-glycylamino-4-hydroxycinnolin-3-yl carboxylate hydrochloride, m.p. over 300° C.

The benzyloxyarbonylglycyl compound used as starting material was obtained as follows:

A solution of benzyloxycarbonylglycine 2,4,5-trichlorophenyl ester (3.1 g.) and ethyl 6-amino-4-hydroxycinnolin-3-yl carboxylate (0.93 g.) in dimethylformamide (10 ml.) was kept at 100° C. for 72 hours. The solution was poured into ether (500 ml.). The precipitated solid was filtered off and washed successively with N-hydrochloric acid and water. The solid was recrystallised from a mixture of ethanol and water to give ethyl 6-benzyloxycarbonylglycylamino-4-hydroxycinnolin-3-yl carboxylate, m.p. 247°–249° C.

EXAMPLE 4

Benzyl chloroformate (7.5 g.) was added to a stirred solution of ethyl 6-amino-4-hydroxycinnolin-3-yl carboxylate (4.66 g.) in pyridine (75 ml.). The solution was stirred for 18 hours at room temperature and for 2 hours at 100° C. The solution was cooled and was poured onto a mixture of ice (500 g.) and 5N-hydrochloric acid (200 ml.). The pale solid which was precipitated was filtered off, washed with water, and recrystallised from a mixture of ethanol and water to give ethyl 6-benzyloxycarbonylamino-4-hydroxycinnolin-3-yl carboxylate, m.p. 250°–252° C.

EXAMPLE 5

In a similar manner to that described in Example 4, and using the appropriate starting materials, there was obtained ethyl 6-(2,2,2-trichloroethoxycarbonyl)amino-4-hydroxycinnolin-3-yl carboxylate, m.p. 251°–253° C.

EXAMPLE 6

Acetyl chloride (0.6 ml.) was added to a stirred solution of ethyl 6-amino-4-hydroxycinnolin-3-yl carboxylate (0.932 g.) in dry pyridine (20 ml.). The solution was stirred at room temperature for 16 hours and then was poured onto a mixture of ice (100 g.) and 5N-hydrochloric acid (50 ml.). The mixture was kept at 4° C. for 4 hours, and the solid precipitate was then filtered off, washed with water (10 ml.), dried as much as possible on the filter, and recrystallised from ethanol to give ethyl 6-acetylamino-4-hydroxycinnolin-3-yl carboxylate, m.p. 280°–281° C.

EXAMPLES 7 and 8

In a similar manner to that described in Example 6, and using the appropriate starting materials, the following compounds were obtained:

ethyl 6-benzoylamino-4-hydroxycinnolin-3-yl carboxylate, m.p. 282°–283° C. (Example 7)

ethyl 6-palmitoylamino-4-hydroxycinnolin-3-yl carboxylate, m.p. 238°–240° C. (Example 8)

EXAMPLE 9

A solution of 6-amino-4-hydroxycinnolin-3-yl carboxylic acid (1.0 g.) in 98% w/v formic acid (2.0 ml.) and 40% w/v formaldehyde in water (2.0 ml.) was heated under reflux on a steam bath for 8 hours. The solution was cooled in ice. The solid which separated was filtered off, washed with methanol and dried to give 6-dimethylamino-4-hydroxycinnolin-3-yl carboxylic acid, m.p. over 330° C.

EXAMPLE 10

A suspension of ethyl 6-amino-4-hydroxycinnolin-3-yl carboxylate (1.164 g.) in water (10 ml.) and concentrated hydrochloric acid (1.0 ml.) was stirred at 0° C. in an ice-salt bath, and a solution of sodium nitrite (0.5 g.) in water (3 ml.) was added during 5 minutes, maintaining the temperature at 0°–5° C. The mixture was stirred at 0° C. for 10 minutes, and this mixture was then added dropwise to a stirred solution of cuprous cyanide (0.54 g.) and sodium cyanide (0.6 g.) in water (4 ml.), heated at 60°–70° C. on a steam bath. The mixture was heated under reflux for 30 minutes. The brown solid which was precipitated was filtered off, washed thoroughly with water and dried as much as possible on the filter. The crude product was extracted with boiling ethanol (2 × 100 ml.), and the combined extracts were filtered and the filtrate evaporated under reduced pressure. The residue was applied to a column of silica (30 g., Kieselgel 60). Elution with a mixture containing 15% v/v of ethanol and 85% v/v of chloroform yielded ethyl 6-cyano-4-hydroxycinnolin-3-yl carboxylate, m.p. 259°–261° C.

EXAMPLE 11

A suspension of ethyl 6-cyano-4-hydroxycinnolin-3-yl carboxylate (0.243 g.) in N-sodium hydroxide solution (10 ml.) and 5% v/v hydrogen peroxide in water (1 drop) was heated on a steam bath for 4 hours. The solution was filtered and the filtrate was acidified to pH 2 with 3N-hydrochloric acid. The mixture was cooled in ice. The solid which separated was filtered off, washed thoroughly with water and dried to give 4-hydroxycinnolin-3,6-yl dicarboxylic acid, m.p. over 330° C.

EXAMPLE 12

A suspension of ethyl 6-amino-4-hydroxycinnolin-3-yl carboxylate hydrochloride (1.164 g.) in water (10 ml.) and concentrated hydrochloric acid (1.0 ml.) was stirred at 0° C. in an ice-salt bath, and a solution of sodium nitrite (0.5 g.) in water (3 ml.) was added during 5 minutes, maintaining the temperature at 0°-5° C. The mixture was stirred for 10 minutes at 0° C., and then magnesium sulphate (0.020 g.), furan (20 ml.) and sodium acetate trihydrate (4 g.) were added. The reaction mixture was stirred vigorously, allowed to warm to room temperature and stirred vigorously for 48 hours. The mixture was extracted with ethyl acetate (4 × 100 ml.). The combined extracts were washed with water, dried ($MgSO_4$), filtered, and evaporated under reduced pressure. The oily brown residue was dissolved in ethyl acetate and applied to a silica column (30 g., Kieselgel 60). Elution with ethyl acetate yielded ethyl 6-furyl-4-hydroxycinnolin-3-yl carboxylate, m.p. 198°-200° C.

EXAMPLES 13 and 14

In a similar manner to that described in Example 12, and using the appropriate starting materials, the following compounds were obtained:

ethyl 4-hydroxy-6-pyridylcinnolin-3-yl carboxylate, m.p. 260°-262° C. (Example 13)
ethyl 6-(ethoxycarbonylphenyl)-4-hydroxycinnolin-3-yl carboxylate, m.p. 180° C. (Example 14)

EXAMPLE 15

A solution of p-toluenesulphonyl chloride (7.0 g.) in ether (30 ml.) was added to a stirred solution of 6-amino-4-hydroxycinnolin-3-yl carboxylic acid (1.025 g.) in N-sodium hydroxide solution (15 ml.). The heterogeneous mixture was stirred vigorously for 16 hours. The aqueous phase was separated, washed with ether (2 × 25 ml.), and acidified to pH 2 with 5N-hydrochloric acid. The solid which separated was filtered off, washed with water and dried as much as possible on the filter. The product was purified by chromatography on a silica column (30 g., Kielselgel 60), eluted with a mixture of ethanol (15 parts by volume), chloroform (85 parts by volume) and formic acid (1 parts by volume), to give 4-hydroxy-6-(p-toluenesulphonylamino)cinnolin-3-yl carboxylic acid, m.p. 272°-273° C.

EXAMPLE 16

Styrene oxide (4 g.) was added to a hot solution of ethyl 6-amino-4-hydroxycinnolin-3-yl carboxylate (1.17 g.) in ethanol (100 ml.). The solution was kept at room temperature overnight and was then heated under reflux on a steam bath for 8 hours. The solution was evaporated under reduced pressure. The oily residue was dissolved in ethanol (100 ml.), and the solution boiled with charcoal (2 g.) for 5 minutes, filtered hot, and hot water (150 ml.) added to the filtrate. On cooling, a red solid separated which was filtered off. On evaporation of the filtrate to approximately 150 ml., a yellow solid separated which was filtered off. This solid was dissolved in ethanol (20 ml.), silica (5 g., Kieselgel 60) was added, the ethanol was evaporated and the residue applied to the top of a column of silica (100 g., Kiesegel 60). Elution with a mixture of 15% v/v ethanol and 85% v/v chloroform, and evaporation of the appropriate fractions yielded crystalline ethyl 4-hydroxy-6-(2-hydroxy-2-phenethylamino)cinnolin-3-yl carboxylate, m.p. 236°-238° C.

EXAMPLE 17

1-Isocyanato-1-methoxycarbonyl-2-phenylethane (1.2 g.) was added to a stirred solution of ethyl 6-amino-4-hydroxycinnolin-3-yl carboxylate (1.17 g.) in pyridine (20 ml.). The mixture was stirred overnight and the solid which separated was washed successively with pyridine (10 ml.) and ether (100 ml.). The solid was dissolved in boiling ethanol (1 l.), and the solution was filtered whilst hot. The filtrate was evaporated to approximately 300 ml. After standing at 0° C. overnight, the mixture was filtered and the solid residue washed successively with ethanol (50 ml.) and ether (100 ml.) to give ethyl 4-hydroxy-6-[3-(α-methoxycarbonylphenethyl)ureido]cinnolin-3-yl carboxylate, m.p. 242°-243° C.

EXAMPLE 18

Phenyl isothiocyanate (1.1 ml.) was added to a solution of ethyl 6-amino-4-hydroxycinnolin-3-yl carboxylate (0.932 g.) in dry pyridine (20 ml.). The mixture was stirred at room temperature for 18 hours, during which time a yellow solid slowly precipitated. The solid was filtered off and washed successively with N-hydrochloric acid (10 ml.), water (25 ml.), dry ethanol (25 ml.) and dry ether (25 ml.). The crude product was applied to a silica column (100 g. of Kieselgel 60) and eluted with a 15% v/v mixture of dry ethanol and chloroform. Evaporation of the appropriate fractions gave ethyl 4-hydroxy-6-($N^2$-phenylthioureido)cinnolin-3-yl carboxylate, m.p. 260° C.

EXAMPLE 19

Amyl nitrate (1 ml.) was added to a stirred suspension of ethyl 6-amino-4-hydroxycinnolin-3-yl carboxylate (1 g.) in thiophen (100 ml.). The suspension was stirred and heated under reflux for 2 hours. The suspension was filtered whilst hot and the filtrate was evaporated, giving a brown crystalline residue. The solid was applied to a silica column (100 g. of Kieselgel 60) and eluted with a 10% v/v mixture of dry ethanol and chloroform. The appropriate fractions were evaporated, and the residue was crystallised from 1:1 v/v aqueous ethanol to give ethyl 4-hydroxy-6-thienylcinnolin-3-yl carboxylate, m.p. 258°-260° C.

EXAMPLE 20

7-Isopropylxanthone-3-carboxylic acid (1.4 g) was dissolved in thionyl chloride (35 ml.) and the solution was heated under reflux until evaporation of gas had ceased. The excess thionyl chloride was evaporated in vacuo and the solid residue suspended in toluene (35 ml.). The toluene was evaporated in vacuo and to the dry solid residue was added a solution of ethyl 6-amino-4-hydroxycinnolin-3-yl carboxylate (1.16 g) in dry pyridine (30 ml.). The mixture was stirred at room temperature for 16 hours, and then heated at 100° C. for 5 hours. The solution was then cooled and poured into a mixture of ice and N-HCl, whereupon a yellow solid was precipitated. The mixture was filtered and the solid residue was crystallised from aqueous dimethylformamide to give ethyl 4-hydroxy-6-(7-isopropylxanthone-3-carbonylamido)cinnolin-3-yl carboxylate, m.p. 295°–7° C.

EXAMPLE 21

To a solution of ethyl 6-amino-4-hydroxycinnolin-3-yl carboxylate (1.0 g.) in dry pyridine (20 ml.) was added o-acetoxybenzoylchloride (0.8 g), and the mixture was stirred at room temperature for 16 hours. The solution was then heated to 100° C. for 1 hr., cooled to 20° C. and poured into a mixture of ice and excess N-HCl. The mixture was filtered and the solid residue crystallised from aqueous ethanol to give ethyl 36-o-acetoxybenzamido-4-hydroxycinnolin-3l -yl carboxylate, m.p. 240°–2° C.

EXAMPLES 22 and 23

In an analogous manner to that described in Example 21 the following compounds were obtained:

ethyl 4-hydroxy-6-(3,4,5-trimethoxybenzamido)cinnolin-3-yl carboxylate, m.p. 267°–9° C. (Example 22)
ethyl 4-hydroxy-6-(4-nitrobenzamido)cinnolin-3-yl carboxylate, m.p. over 300° C. (Example 23)

EXAMPLE 24

To a solution of ethyl 6-amino-4-hydroxycinnolin-3-yl carboxylate (1.0 g.) in dry pyridine (25 ml.) was added 1,1'-thiocarbonyl-di-imidazole (0.76 g.) and carbon disulphide (15 ml.). The mixture was heated to reflux and after a few minutes a yellow solid was seen to precipitate from the clear solution. After 3 hours heating under reflux the mixture was filtered whilst hot and the solid product was washed sucessively with ethanol and ether. After crystallisation from a mixture of dimethylformamide and ethyl acetate, there was obtained $N^1,N^2$-(3-ethoxycarbonyl-4-hydroxycinnolin-6-yl)thiourea, m.p. over 300° C. (decomposition).

EXAMPLE 25

Methanesulphonic anhydride (1.392 g.) was added to a solution of ethyl 6-amino-4-hydroxycinnolin-3-yl carboxylate (0.932 g.) in dry pyridine (20 ml.), and the mixture was stirred at room temperature overnight. The resulting solution was poured into ether (500 ml.) and the amorphous solid which precipitated was filtered off and applied to a silica column (100 g. Kieselgel 60). Elution with a mixture of 15% v/v ethanol and 85% v/v chloroform, and evaporation of the appropriate fractions gave ethyl 4-hydroxy-6-(methanesulphonylamino)cinnolin-3-yl carboxylate, m.p. 274°–5° C.

EXAMPLE 26

A mixture of ethyl 6-amino-4-hydroxycinnolin-3-yl carboxylate (0.932 g.), 5,5-dimethylcyclohexan-1,3-dione (2.24 g.) and p-toluenesulphonic acid (0.4 g.) in ethanol (100 ml.) was heated under reflux on a steam bath for 16 hours. The solution was evaporated in vacuo and the residue was applied to a silica column (100 g. Kieselgel 60). Elution with a mixture of 15% v/v ethanol and 85% v/v chloroform, and evaporation of the appropriate fractions gave crystalline ethyl 6-[(5,5-dimethylcyclohexen-3-one-yl)amino]-4-hydroxycinnolin-3-yl carboxylate, m.p. 274° C.

EXAMPLE 27

A suspension of ethyl 6-amino-4-hydroxycinnolin-3-yl carboxylate (1.165 g.) in water (10 ml.) and concentrated hydrochloric acid (1.5 ml.) was stirred at 0° C. in an ice-salt bath. A solution of sodium nitrite (0.5 g.) in water (3 ml.) was added during 5 minutes, maintaining the temperature at 0°–5° C. The mixture was stirred for 5 minutes at 0° C., and then the diazonium salt solution was filtered and its pH adjusted to 3–5 by addition of aqueous sodium acetate solution (2 g. in 10 ml. water). Furfuraldehyde (0.5 ml.) and cupric chloride (0.13 g.) were then added and the reaction mixture was stirred vigorously, allowed to warm to room temperature, and stirred overnight. The resulting mixture was filtered, and the solid residue was washed with water. Crystallisation from aqueous ethanol gave ethyl 6-(2-aldehydofuryl)-4-hydroxycinnolin-3-yl carboxylate, m.p. over 330° C.

EXAMPLE 28

In an analogous manner to that described in Example 27 there was obtained ethyl 4-hydroxy-6-maleimidocinnolin-3-yl carboxylate, m.p. 257°–260° C.

EXAMPLE 29

A suspension of ethyl 6-amino-4-hydroxycinnolin-3-yl carboxylate (1.165 g.) in water (10 ml.) and concentrated hydrochloric acid (1.5 ml.) was stirred at 0° C. A solution of sodium nitrite (0.5 g.) in water (3 ml.) was added over 5 minutes, maintaining the temperature at 0°–5° C. The resulting solution was stirred for 5 minutes at 0° C., adjusted to pH 3.5 with aqueous sodium carbonate, and then added to a solution of potassium methyl xanthate (1.0 g.) in water (10 ml.) at 60° C. on a steam bath. A yellow solid was immediately precipitated. The mixture was warmed at 60°–70° C. for 10 minutes. The mixture was filtered, and the solid residue washed thoroughly with water and dried on the filter. The product (the corresponding 6-CH$_3$O.CS.S-derivative) was suspended in toluene (100 ml.) and heated under reflux until all gaseous evolution had stopped. The mixture was evaporated in vacuo and the solid residue was crystallised from aqueous ethanol to give ethyl 4-hydroxy-6-thiomethylcinnolin-3-yl carboxylate, m.p. 137° C.

EXAMPLE 30

A suspension of ethyl 4-hydroxy-6-nitrocinnolin-3-yl carboxylate (2.63 g.) and platinum oxide (100 mg.) in a mixture of dry ethanol (20 ml.), acetone (5 ml.) and glacial acetic acid (1 ml.) was stirred at room temperature in an atmosphere of hydrogen until the uptake of hydrogen ceased. Charcoal (0.5 g.) was added, the mixture was heated under reflux for 10 minutes on a steam bath, filtered through celite and evaporated to dryness in vacuo.

The solid residue was crystallized from aqueous ethanol to give ethyl 4-hydroxy-6-isopropylaminocinnolin-3-yl carboxylate, m.p. 170°–1° C.

EXAMPLES 31 TO 34

In an analogous manner to that described in Example 30 there were obtained:
ethyl 6-n-butylamino-4-hydroxycinnolin-3-yl carboxylate, m.p. 170° C. (Example 31),
ethyl 6-n-but-2-ylamino-4-hydroxycinnolin-3-yl carboxylate, m.p. 169° C. (Example 32), ethyl 6-cyclopentylamino-4-hydroxycinnolin-3-yl carboxylate, m.p. 203°–5° C. (Example 33), and
ethyl 6-cyclohexylamino-4-hydroxycinnolin-3-yl carboxylate, m.p. 199°–200° C. (Example 34).

EXAMPLE 35

A mixture of ethyl 6-glycylamino-4-hydroxycinnolin-3-yl carboxylate hydrochloride (0.5 g.) and 30% w/w palladium-on-charcoal catalyst (0.1 g.) in a solution of 40% w/v aqueous formaldehyde (2.5 ml) and water (20 ml.) was shaken overnight at room temperature in an atmosphere of hydrogen.

The suspension was filtered through celite and the filtrate was evaporated in vacuo to give an oily residue. The residue was crystallized from a 50/50 v/v mixture of dry ethanol and ethyl acetate to give ethyl 6-(N,N-dimethylglycylamino)-4-hydroxycinnolin-3-yl carboxylate hydrochloride, m.p. 205° C.

EXAMPLE 36

In a similar manner to that described in Example 5 there was obtained ethyl 6-hexanoylamino-4-hydroxycinnolin-3-yl carboxylate, m.p. 265°–6° C.

EXAMPLES 37 AND 38

In a similar manner to that described in Example 17 there were obtained:

ethyl 6-($N^2$-p-chlorophenylureido)-4-hydroxycinnolin-3-yl carboxylate, m.p. 304° C. (Example 37), and
ethyl 6-[$N^2$-2,4-dibromophenylureido]-4-hydroxycinnolin-3-yl carboxylate, m.p. 302° C. (Example 38).

EXAMPLES 39 – 41

In a similar manner to that described in Example 19 there were obtained:

ethyl 6-(2-chloropyridyl)-4-hydroxycinnolin-3-yl carboxylate, m.p. 172°–5° C. (Example 39),
ethyl 4-hydroxy-6-nitrophenylcinnolin-3-yl carboxylate, m.p. 210° C. (Example 40), and
ethyl 4-hydroxy-6-(4-methylpyridyl)cinnolin-3-yl carboxylate, m.p. 175° C. (Example 41)

EXAMPLE 42

Nitromethane (0.3 ml.) was added to a solution of sodium hydroxide (0.67 g.) in water (10 ml.), maintaining the temperature at 25°–30° C. The solution was warmed to 40° C. and further nitromethane (0.3 ml.) was added at 40°–45° C. The solution was then warmed at 50°–55° C. for 3 minutes, cooled to room temperature by the addition of ice and acidified with concentrated hydrochloric acid (1.5 ml.). The resulting solution of methazonic acid (HO.N=CH.CH$_2$.NO$_2$) was added immediately to a stirred suspension of ethyl 6-amino-4-hydroxycinnolin-3-yl carboxylate (1.16 g.) in N-hydrochloric acid (5 ml.), and the overnight. was stirred at room temperature overnite. The mixture was filtered, and the solid residue was washed free from acid by means of water and then crystallised from aqueous dimethylsulphoxide to give ethyl 4-hydroxy-6-(2-nitroethylenylamino)cinnolin-3-yl carboxylate, m.p. 260°–3° C.

EXAMPLE 43

A mixture of ethyl 6-benzyloxycarbonyl-D-alanylamino-4-hydroxycinnolin-3-yl carboxylate (0.61 g.), 30% w/w palladium-on-charcoal catalyst (0.1 g.), N-hydrochloric acid (1.4 ml.), ethanol (150 ml.) and water (70 ml.) was shaken in an atmosphere of hydrogen for 5 hours. The mixture was filtered through celite (10 g.) and the filtrate was evaporated under reduced pressure. The residual solid was dissolved in water and freeze-dried to give ethyl 6-D-alanylamino-4-hydroxycinnolin-3-yl carboxylate hydrochloride, m.p. 276°–8° C.

The benzyloxycarbonyl-D-alanyl compound used as starting material was obtained as follows:

A solution of benzyloxycarbonyl-D-alanine (1.12 g.) and ethyl 6-amino-4-hydroxycinnolin-3-yl carboxylate (1.16 g.) in pyridine (35 ml.) was stirred as N,$N^1$-dicyclohexylcarbodiimide (1.13 g.) was added. The mixture was allowed to stand for 60 hours, and was then filtered. The filtrate was poured into diethyl ether (1 l.). The solid which separated was filtered off and was then mixed thoroughly with silica (3 g., Kieselgel 60). This mixture was applied to the top of a column of silica (60 g., Kieselgel 60). Elution with a mixture of 15% v/v ethanol and 85% v/v chloroform, and evaporation of the appropriate fractions, yielded crystalline ethyl 6-benzyloxycarbonyl-D-alanylamino-4-hydroxycinnolin-3-yl carboxylate, m.p. 263°–265° C., after recrystallisation from a mixture of ethyl acetate (25 ml.) and petroleum ether (b.p. 60°–80° C., 70 ml.).

EXAMPLES 44 – 48

In a similar manner to that described in Example 42, and using the appropriate starting materials, the following compounds were obtained:

ethyl 4-hydroxy-6-L-valylaminocinnolin-3-yl carboxylate hydrochloride, m.p. 280°–282° C. (Example 44),
ethyl 4-hydroxy-6-L-phenylalanylaminocinnolin-3-yl carboxylate hydrochloride, m.p. 229°–232° C. (Example 45),
ethyl 6-L-aspartylamino-4-hydroxycinnolin-3-yl carboxylate hydrochloride, m.p. 250°–260° C. (decomposition) (Example 46),
ethyl 6-β-alanylamino-4-hydroxycinnolin-3-yl carboxylate hydrochloride, m.p. over 300° C. (decomposition) (Example 47), and
ethyl 4-hydroxy-6-D-phenylglycylaminocinnolin-3-yl carboxylate hydrochloride, m.p. 265°–270° C. (decomposition) (Example 48).

The following starting materials used in Examples 44–48 were prepared in a similar manner to that described for the corresponding compound in Example 43:

ethyl 6-benzyloxycarbonyl-L-valylamino-4-hydroxycinnolin-3-yl carboxylate, m.p. 241°–245° C.
ethyl 6-benzyloxycarbonyl-L-phenylalanylamino-4-hydroxycinnolin-3-yl carboxylate, m.p. 191°–193° C.
ethyl 6-(benzyloxycarbonyl-β-benzyl-L-aspartyl-)amino-4-hydroxycinnolin-3-yl carboxylate, m.p. 165°–166° C.
ethyl 6-benzyloxycarbonyl-β-alanylamino-4-hydroxycinnolin-3-yl carboxylate, m.p. 258°–260° C.
ethyl 6-benzyloxycarbonyl-D-phenylglycylamino-4-hydroxycinnolin-3-yl carboxylate, m.p. 236°–240° C. (decomposition).

EXAMPLE 49

A mixture of ethyl 4-hydroxy-6-isopropylaminocinnolin-3-yl carboxylate (10 g.), maize starch (65 g.), calcium phosphate (130 g.) and magnesium stearate (1 g.)

was compressed, and the compressed mixture was then broken down into granules by passage through a 16-mesh screen. The resulting granules were then compressed into tablets each containing 25 mg. of the active ingredient.

What we claim is:

1. A cinnoline derivative selected from the group consisting of ethyl 6-cyclopentylamino-4-hydroxycinnolin-3-yl carboxylate, ethyl 4-hydroxy-6-isopropylaminocinnolin-3-yl carboxylate, ethyl 4-hydroxy-6-L-phenylalanylaminocinnolin-3-yl carboxylate and ethyl 4-hydroxy-6-thienylcinnolin-3-yl carboxylate, and pharmaceutically-acceptable acid-addition salts thereof.

2. A compound as claimed in claim 1 which is ethyl 4-hydroxy-6-thienylcinnolin-3-yl carboxylate or a pharmaceutically-acceptable acid-addition salt thereof.

3. A compound as claimed in claim 1 which is ethyl 6-cyclopentylamino-4-hydroxycinnolin-3-yl carboxylate or a pharmaceutically-acceptable acid-addition salt thereof.

4. A compound as claimed in claim 1 which is ethyl 4-hydroxy-6-isopropylaminocinnolin-3-yl carboxylate or a pharmaceutically-acceptable acid-addition salt thereof.

5. A compound as claimed in claim 1 which is ethyl 4-hydroxy-6-L-phenylalanylaminocinnolin-3-yl carboxylate or a pharmaceutically-acceptable acid-addition salt thereof.

* * * * *